United States Patent

Ofori

[11] Patent Number: 6,143,937
[45] Date of Patent: Nov. 7, 2000

[54] RECOVERY OF HYDROXYAROMATIC COMPOUND FROM AQUEOUS EXTRACT SOLUTIONS

[75] Inventor: John Yaw Ofori, Niskayuna, N.Y.

[73] Assignee: General Electric Company, Schenectady, N.Y.

[21] Appl. No.: 09/215,387

[22] Filed: Dec. 18, 1998

[51] Int. Cl.⁷ .................................................. C07C 37/72
[52] U.S. Cl. ............................................................. 568/749
[58] Field of Search .............................................. 568/749

[56] References Cited

U.S. PATENT DOCUMENTS

| | | | |
|---|---|---|---|
| 3,155,734 | 11/1964 | Merkel | 568/749 |
| 4,152,528 | 5/1979 | Strahorn | 568/749 |
| 4,187,242 | 2/1980 | Chalk . | |
| 4,374,383 | 2/1983 | Aneja | 568/749 X |
| 4,418,221 | 11/1983 | Yasuda et al. | 568/749 X |
| 5,231,210 | 7/1993 | Joyce et al. . | |
| 5,284,964 | 2/1994 | Pressman et al. . | |
| 5,399,734 | 3/1995 | King, Jr. et al. . | |
| 5,498,789 | 3/1996 | Takagi et al. . | |
| 5,760,272 | 6/1998 | Pressman et al. . | |

FOREIGN PATENT DOCUMENTS 0 633 241 A1  1/1995  European Pat. Off. .

OTHER PUBLICATIONS

"Science and Practice of Liquid–Liquid Extractions", vols. 1 and 2, edited by John D. Thornton, Clarendon Press, Oxford (1992).

*Primary Examiner*—Michael G. Ambrose
*Attorney, Agent, or Firm*—Mike W. Crosby; Noreen C. Johnson

[57] ABSTRACT

A method for efficiently recovering a hydroxyaromatic compound from aqueous extract streams of diaryl carbonate reaction mixtures, comprises contacting the aqueous extracts with a suitable solvent, preferably diphenyl carbonate or anisole. The aqueous stream may then be further recycled or reclaimed, and the hydroxyaromatic compound isolated from the solvent for disposal or further use.

11 Claims, No Drawings

RECOVERY OF HYDROXYAROMATIC COMPOUND FROM AQUEOUS EXTRACT SOLUTIONS

BACKGROUND OF THE INVENTION

The present invention relates to a method for recovering a hydroxyaromatic compound from aqueous extract streams. In particular, this invention relates to methods for recovering a hydroxyaromatic compound from aqueous extract streams generated in the production of diaryl carbonates.

Diaryl carbonates, and diphenyl carbonate in particular, are valuable monomer precursors for the preparation of polycarbonates by melt transesterification. An advantageous route for the synthesis of diaryl carbonates is the direct carbonylation of hydroxyaromatic compounds by carbon monoxide and an oxidant in the presence of a catalyst.

A wide range of catalysts may be used in this preparation of diaryl carbonates. For example, U.S. Pat. No. 4,187,242 to Chalk discloses catalysts derived from Group VIIIB metals, i.e., metals selected from the group consisting of ruthenium, rhodium, palladium, osmium, iridium and platinum, or complexes thereof. U.S. Pat. Nos. 5,231,210 to Joyce, et al., 5,284,964 and 5,760,272 to Pressman et al., and 5,399,734 to King, Jr., et al. further disclose the use of co-catalysts, including metal co-catalyst species such as cobalt pentadentate complexes and complexes of cobalt with pyridines, bipyridines, terpyridines, quinolines, isoquinolines, aliphatic polyamines such as ethylenediamine, crown ethers, aromatic or aliphatic amine ethers such as cryptands, and Schiff bases, in combination with organic co-catalysts such as terpyridines and quaternary ammonium or phosphonium halides. In U.S. Pat. No. 5,498,789 to Takagi et al., the catalyst system consists of a palladium compound, at least one lead compound, at least one halide selected from quaternary ammonium halides and quaternary phosphonium halides, and optionally at least one copper compound.

As can be seen from the above brief review, the crude reaction mixtures arising from the production of diaryl carbonates can contain complex mixtures of catalyst and co-catalyst metals, and organic products and by-products. The cost of commercially implementing direct oxidative carbonylation is heavily dependent on a combination of the efficiency of the catalyst package and on the ability to reclaim and recycle the expensive catalyst components and unconverted hydroxyaromatic starting material, in particular phenol.

It has been found that aqueous solvent extraction of crude diphenyl carbonate mixtures gives rise to an aqueous extract stream containing from about 0.5 to about 20% phenol, and between about 80% to about 99% water. The aqueous stream may further comprise metals, water-soluble organic materials, including other hydroxyaromatic compounds in addition to phenol, and any extractants (e.g., salts, acids, or complexing agents) added to the original aqueous extract. The presence of phenol in these aqueous extract streams may interfere with subsequent manipulations of the stream, for example by impeding phase separation. The presence of phenol starting material and other hydroxyaromatic compounds formed as by-products or present as impurities further complicates disposal of the stream. Methods for the recovery of a hydroxyaromatic compound from such aqueous extract streams would therefore be both financially and environmentally desirable.

SUMMARY OF THE INVENTION

The above-discussed and other drawbacks and deficiencies of the art are alleviated by the method of the present invention for the recovery of a hydroxyaromatic compound from an aqueous extract stream generated in diaryl carbonate production, comprising extracting the aqueous extract stream with a solvent essentially immiscible with water and in which a hydroxyaromatic compound is soluble, thereby effecting transfer of hydroxyaromatic compound from the aqueous extract stream into the solvent. Implementation of the method of this invention substantially reduces both economic and environmental concerns in the preparation of diaryl carbonates. The process is particularly useful for the recovery of phenol from an aqueous extract stream generated in diphenyl carbonate production.

DETAILED DESCRIPTION OF THE INVENTION

Hydroxyaromatic compound as used in the present invention refers to at least one hydroxyaromatic compound present in a process stream from diaryl carbonate production. The hydroxyaromatic compound comprises the hydroxyaromatic starting material used in the diaryl carbonate production process and any hydroxyaromatic compounds which may be present in a process stream from diaryl carbonate production as by-products or impurities. Such by-products and impurities may include, but are not limited to, coupled hydroxyaromatic compounds comprising compounds with more than one aromatic ring, and halogenated hydroxyaromatic compounds and halogenated coupled hydroxyaromatic compounds. The hydroxyaromatic starting material preferably comprises at east 90%, more preferably greater than 95%, and most preferably greater than 99% by weight of the mixture of hydroxyaromatic compounds present in the aqueous extract stream arising from any diaryl carbonate production process.

The present invention makes possible efficient recovery of hydroxyaromatic starting material from aqueous extracts of crude mixtures resulting from the production of diaryl carbonates, preferably diphenyl carbonate. The method comprises treating an aqueous extract stream from the production of diaryl carbonates with a suitable solvent by liquid—liquid extraction. The aqueous stream may then be further recycled or reclaimed, and the hydroxyaromatic starting material may be isolated from the solvent for further use.

Solvent extraction of crude diphenyl carbonate mixtures with an aqueous solution gives rise to an aqueous stream containing between about 0.5 to about 20% phenol starting material and between about 80% and about 99% water. Depending on extraction conditions, the aqueous extract stream may further comprise extracted catalyst and co-catalyst components, as well as water-soluble organic components, including other hydroxyaromatic compounds, and added extractants such as acids, bases, salts, surfactants, or chelating agents. In accordance with the method of the present invention, phenol is removed from these or other phenol-containing aqueous extract streams of the diphenyl carbonate process by solvent extraction using a suitable solvent.

Depending upon the reaction conditions in diphenyl carbonate production, minor amounts of other hydroxyaromatic compounds may be present in the aqueous extract stream along with phenol starting material. These other hydroxyaromatic compounds, such as biphenols and halogenated phenols, may also be recovered along with phenol in the solvent extraction process, depending upon their relative solubilities in water and the extracting solvent. It should be understood that phenol starting material is the predominant hydroxyaromatic compound in any mixture of hydroxyaromatic compounds obtained in an aqueous extract stream from diphenyl carbonate production. Phenol preferably comprises at least 90%, more preferably greater than 95%, and most preferably greater than 99% by weight of the total amount of hydroxyaromatic compounds present in the aqueous extract.

Suitable solvents for extraction of aqueous extract streams from diphenyl carbonate production include those which are essentially immiscible with water and which have a high solubility for phenol at the extraction temperature. Preferably, phenol is 95% or more soluble in the solvent, and water is less than 5% soluble in the solvent at the extraction temperature. Even more preferably, phenol is completely soluble in the solvent, and water is less than I % soluble in the solvent at the extraction temperature. The temperature of the extraction may be adjusted in order to increase the solubility of phenol in the solvent. The solvents are preferably stable in the presence of acid, most preferably stable in the presence of an aqueous solution having between about 1% and about 20% of hydrochloric acid by weight (or a solution having equivalent acidity).

Such solvents include, but are not restricted to anisole and diphenyl carbonate. Diphenyl carbonate is preferred for extractions at temperatures above 80° C., and is preferably used for extraction at temperatures between about 80° C. and about 110° C. Above 80° C., diphenyl carbonate is completely miscible with phenol, whereas water solubility of diphenyl carbonate is less than 1 percent. Anisole is preferred for extractions at temperatures between about 5° C. and about 80° C. or higher (including room temperature), because of its low freezing point (−37.3° C. for pure anisole). Anisole is miscible with phenol in the temperature ranges of interest, and water solubility in anisole is about 1000 ppm at room temperature.

Methods of liquid-liquid extraction are well known in the art, being described, for example in "Science and Practice of Liquid—Liquid Extractions," Vols. 1 and 2, edited by John D. Thornton, Clarendon Press, Oxford (1992), particularly volume 1, pp. 492–589 which are incorporated by reference herein. Generally, liquid-liquid extraction is effected by washing through an aqueous extract that amount of solvent effective to cause phenol to migrate out of the aqueous phase and into the extractant (solvent) phase, employing any of a number of contacting devices, such as a mixer-settler unit, an agitated column, or similar device, in a batch, semi-continuous, or continuous process. The amount of aqueous stream extracted, amount of solvent used, number of washings, and length of time required for each wash are empirically determined, depending on such factors as the solubility of phenol in the solvent, the miscibility of the solvent with water, the temperature of the extraction, the cost of the solvent, disposal requirements of the solvent, the required degree of phenol removal from the aqueous stream, the mixing efficiency between the two phases, the ease of phase separation, and like concerns. Balancing of such considerations to maximize efficiency and/or removal, in addition to transfer of this information from laboratory testing to a continuous or batch operation on a large scale, taking into account phase densities and fluid dynamic considerations, is well within the skills of a practitioner in the art.

While the above method is directed to the removal of phenol from aqueous extract streams derived from reaction mixtures arising from diphenyl carbonate production, it is to be recognized that the method may be employed to recover different hydroxyaromatic compounds from aqueous extract streams derived from other diaryl carbonate processes, provided that the requisite conditions of miscibility of hydroxyaromatic compounds with the extracting solvent, and immiscibility of the extracting solvent with water are met. Preferably, the hydroxyaromatic starting material is 95% or more soluble in the solvent, and water is less than 5% soluble in the solvent at the extraction temperature. Even more preferably, the hydroxyaromatic starting material is completely soluble in the solvent, and water is less than 1% soluble in the solvent at the extraction temperature.

Such other diaryl carbonate processes may employ as starting materials hydroxyaromatic compounds including monocyclic, polycyclic or fused polycyclic aromatic monohydroxy or polyhydroxy compounds having from 6 to 30, and preferably from 6 to 15 carbon atoms. Illustrative hydroxyaromatic compounds include, but are not limited to, phenol, cresol, xylenol, resorcinol, hydroquinone, naphthol, catechol, cumenol, the various isomers of dihydroxynaphthalene, bis(4-hydroxyphenyl)propane-2,2, α,α'-bis(4-hydroxyphenyl)p-diisopropylbenzene, and bisphenol A. Aromatic organic monohydroxy compounds are particularly preferred, with phenol being the most preferred.

The following examples are provided by way of example only, and should not be read to limit the scope of the invention. All phenol % values are weight % values based on the liquid phase in which the phenol is present.

EXAMPLE 1

55.2 g of aqueous extract of a crude diphenyl carbonate reaction mixture, containing 4.06% phenol and no diphenyl carbonate, was extracted with 11.8 g of anisole at 25° C. After the single extraction, the aqueous layer contained 1.14% phenol as determined by liquid chromatography.

EXAMPLE 2

937.4 g of aqueous extract of a crude diphenyl carbonate reaction mixture, containing 4.13% phenol and no diphenyl carbonate, was extracted with 300.5 g of anisole at 25° C. After extraction was complete, with the two phases still in contact with each other, the phenol level in the aqueous phase was 0.8%, while the anisole phase contained 10.87% phenol. Then, 811.6 g of untreated aqueous extract was added to the system, allowed to equilibrate, and then phase separated (1688.62 g total aqueous phase, 360.88 g anisole phase). The aqueous phase was then separated and extracted with 301.6 g of fresh anisole. The mass of the second anisole phase after this extraction was 314.5 g, and that of the aqueous phase was 1673.4 g. The aqueous phase after this extraction contained 0.19% phenol, while the anisole phase contained 4.12% phenol.

EXAMPLE 3

196.2 g of aqueous extract of a crude diphenyl carbonate reaction mixture, containing 8.14% phenol and no diphenyl carbonate, was extracted with 66.1 g of diphenyl carbonate at 85° C. After extraction, the phenol level in the aqueous extract was 2.07%, while the phenol level in the diphenyl carbonate phase was 15.63% as determined by liquid chromatography.

The extraction solvent containing one or more hydroxyaromatic compounds may be disposed of by standard methods, for example incineration. Also, the hydroxyaromatic starting material contained in the extraction solvent may be isolated from the solvent by standard methods for further use. Such methods may include evaporation of the solvent, crystallization of the hydroxyaromatic starting material, distillation, chromatography, and like isolation and purification methods. In the course of isolation and purification the starting hydroxyaromatic compound may be substantially freed of any other hydroxyaromatic compounds which may be present at the end of the diaryl carbonate production process as by-products or impurities, such as coupled hydroxyaromatic compounds and halogenated hydroxyaromatic compounds.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method of recovering a hydroxyaromatic compound from an aqueous extract stream generated in diaryl carbonate production, said method comprising extracting the aqueous extract stream with a solvent selected from the group consisting of anisole and diphenyl carbonate, thereby effecting transfer of hydroxyaromatic compound from the aqueous extract stream into the solvent.

2. The method of claim 1, wherein the hydroxyaromatic compound comprises the hydroxyaromatic starting material in at least 90% by weight of the total amount of hydroxyaromatic compounds.

3. The method of claim 2, wherein the hydroxyaromatic compound comprises the hydroxyaromatic starting material in greater than 95% by weight of the total amount of hydroxyaromatic compounds.

4. The method of claim 1, wherein the hydroxyaromatic compound is phenol.

5. A method of recovering phenol from an aqueous extract stream of a reaction mixture from the production of diphenyl carbonate, comprising extracting the aqueous extract stream with anisole at temperatures above about 5° C., thereby effecting transfer of phenol from said aqueous extract into said solvent.

6. A method of recovering phenol from an aqueous extract stream of a reaction mixture from the production of diphenyl carbonate, comprising extracting the aqueous extract stream with diphenyl carbonate, thereby effecting transfer of phenol from said aqueous extract into said solvent.

7. The method of claim 6, wherein the extraction temperature is between about 80° C. to about 110° C.

8. The method of claim 1, wherein the solvent is diphenyl carbonate.

9. The method of claim 8, wherein the extraction temperature is between about 80° C. and about 110° C.

10. The method of claim 1, wherein the solvent is anisole.

11. The method of claim 10, wherein the extraction temperature is above about 5° C.

* * * * *